United States Patent [19]

Williams

[11] Patent Number: 4,576,169

[45] Date of Patent: Mar. 18, 1986

[54] COMFORT COLLAR

[76] Inventor: Annie J. Williams, 3015 N. Stockton, Ada, Okla. 74820

[21] Appl. No.: 634,746

[22] Filed: Jul. 26, 1984

[51] Int. Cl.⁴ .................................................. A61F 7/10
[52] U.S. Cl. ...................................... 128/402; 62/530; 128/403
[58] Field of Search ............... 128/380, 384, 402, 403; 62/530; 126/204

[56] References Cited

U.S. PATENT DOCUMENTS

| | | | |
|---|---|---|---|
| 1,567,931 | 12/1925 | Epler | 128/402 |
| 2,288,745 | 7/1942 | Sammis | 128/403 |
| 3,815,610 | 6/1974 | Winther | 128/402 X |
| 4,055,188 | 10/1977 | Pelton | 128/403 X |
| 4,326,533 | 4/1982 | Henderson | 128/402 |
| 4,372,318 | 2/1983 | Viesturs et al. | 128/402 X |

Primary Examiner—Anton O. Oechsle

[57] ABSTRACT

An improved collar is provided which can be worn around the neck of an individual to assist in cooling the individual, especially when the individual is subjected to high ambient heat conditions. The improved collar comprises an elongated, pliable insulation member adapted to substantially encompass and form a continuous collar about the neck of the wearer, a towel member substantially enclosing the insulation member, and at least one cooling packet supported by the towel member so as to be positioned between the insulation member and the wearer's neck and thereby cooling the entire body of the wearer.

8 Claims, 8 Drawing Figures

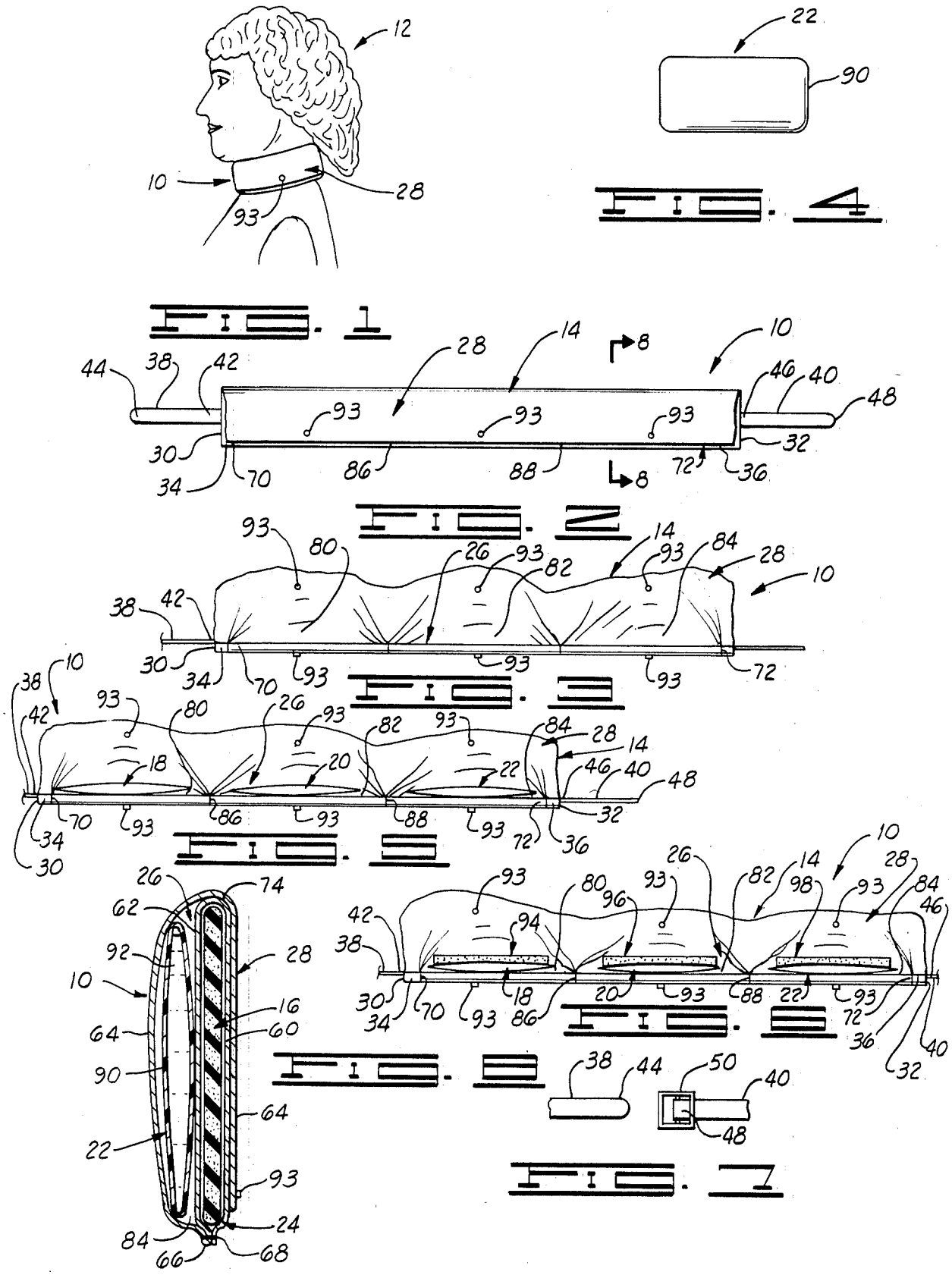

COMFORT COLLAR

BACKGROUND OF THE INVENTION

1. Field of the Invention

The present invention relates to a body cooling device and more particularly, but not by way of limitation, to an improved collar adapted to be comfortably worn about the neck of a person subjected to high ambient heat conditions.

2. Description of Prior Art

Workers in industry are often subjected to high ambient heat conditions during the work period. Because of the type of work being performed, the design of the facilities and the equipment employed by the workers, the form of cooling available to improve the comfort of the workers is very limited. In many instances the only form of cooling available to the workers is generated by large fans which blow hot air across the facilities and thus do not serve to dissipate the heat from the worker's body. It would be desirable to provide workers subjected to high ambient temperatures with a means for lowering the body temperature. If such means were available the efficiency and output of the worker would be increased. However, no suitable means have heretofore been known for effectively lowering the body temperature of workers other than through the use of air conditioning which is ineffective in many facilities, either due to the size of the facilities or the nature of the work being carried out in such facilities. Thus, a need has long been recognized for an efficient, inexpensive device which can be worn by a person subjected to high ambient heat conditions and which is capable of dissipating the heat from the person's body so that the person remains substantially cool and comfortable while performing their work task.

SUMMARY OF THE INVENTION

According to the present invention an improved collar is provided which can be comfortably worn about the neck of a person subjected to high ambient heat conditions to effectively and efficiently lower the body temperature of the person. Broadly, the improved collar comprises an elongated, pliable insulation member adapted to substantially encompass and form a continuous collar about the neck of the wearer, a towel member substantially enclosing the insulation member, and at least one cooling packet supported by the towel member so as to be disposed between the insulation member and the wearer's neck so as to provide a comfort zone, to dissipate heat from the wearer's neck, and thereby cool the entire body of the wearer. More specifically, the towel member is a unitary body member characterized as having a first side portion, a medial portion and a second side portion. The first side portion and the medial portion are connected along a lower, adjacently disposed longitudinally extended edge so as to define a first and second cavity within the body member. The insulation member is disposed within the first cavity member such that the body member substantially encapsulates the insulation member. The second side portion of the body member, which commences at the union of the first side portion and the medial portion, is moveable between a first position and a second position. In the first position the second side portion extends in a direction away from the first side portion and permits access to the second cavity for placement of cooling packets within the second cavity; whereas in the second position the second side portion is disposed substantially adjacent the first side portion so as to substantially close off the second cavity and secure the cooling packets within the second cavity.

An object of the present invention is to provide a device for dissipating the heat from a person's body when the person is subjected to high ambient heat conditions.

Another object of the present invention, while achieving the above stated object, is to provide an improved cooling device which can readily be worn without substantially restricting the movement of the individual or the parts of the body to which the cooling device is secured.

Another object of the present invention, while achieving the above stated objects, is to provide an improved comfort collar capable of dissipating heat from a person's body which is attractive in appearance, easy to use, and economical to manufacture.

Other objects, advantages and features of the present invention will be apparent to those skilled in the art from the following detailed description when read in conjunction with the drawings and appended claims.

BRIEF DESCRIPTION OF THE DRAWINGS

FIG. 1 is a view of a comfort collar of the present invention positioned around a person's neck.

FIG. 2 is a side elevational view of the comfort collar of the present invention illustrated in an extended position and illustrating a closure flap in a closed position.

FIG. 3 is a top elevational view of the comfort collar of the present invention illustrating the closure flap portion of the comfort collar in an extended position and illustrating a plurality of cavity segment portions adapted to receive a cooling packet.

FIG. 4 is a side elevational view of a cooling packet positionable within each of the cavity segment portions of the comfort collar illustrated in FIG. 3.

FIG. 5 is a top elevational view of the comfort collar having the closure flap in an extended position and illustrating a plurality of cooling packets disposed within the cavity segment portions of the comfort collar.

FIG. 6 is a top elevational view of the comfort collar of the present invention having the closure flap in an extended position and illustrating a plurality of insulation insert members positioned substantially adjacent the cooling packets disposed within the cavity segment portions of the comfort collar.

FIG. 7 is another embodiment of a fastening assembly for connecting the comfort collar around a person's neck.

FIG. 8 is an enlarged cross sectional view of the comfort collar of FIG. 2 taken along the line 8—8.

DESCRIPTION OF PREFERRED EMBODIMENTS

Referring to the drawings and more particularly to FIG. 1, a comfort collar 10 constructed in accordance with the present invention is illustrated disposed about the neck of a person 12. The comfort collar 10 which permits cooling of the neck of a person subjected to high ambient heat conditions, and thus provided a comfort level for the entire body of the person 12 wearing the comfort collar 10, is constructed of a water-absorbent textile material, such as a towel, which is non-irritating to human skin.

As more clearly illustrated in FIGS. 2, 3, 5, 6, and 8, the comfort collar 10 comprises a unitary body member 14, such as a towel, an elongated insulation member 16 (see FIG. 8), and a plurality of coolant containing packets 18, 20 and 22. The elongated insulation insert member 16, which functions as a support and forming member for the unitary body member 14 can be fabricated of any pliable material, such as foam rubber and the like. The unitary body member 14 is fabricated so as to contain an internally disposed first elongated cavity 24 adapted to receive and substantially encapsulate the elongated insulation member 16, an internally disposed second elongated cavity 26 adapted to receive the plurality of coolant containing packets 18, 20 and 22, and a fold-over flap or closure member 28. The first and second elongated cavities 24, 26 extend substantially the length of the unitary body member 14 and terminate a select distance from ends 30, 32 of the unitary body member 14 so as to provide the unitary body member 14 with end flap portions 34 and 36.

In order to secure the unitary body member 14 of the comfort collar 10 around the neck of the person 12, the comfort collar 10 further comprises a collar fastening mechanism, such as collar fastening straps 38 and 40. The collar fastening strap 38, an elongated member, is provided with a first end 42 and an opposed second end 44; and the collar fastening strap 40, also an elongated member, is provided with a first end 46 and an opposed second end 48. The first end 42 of the collar fastening strap 38 is secured to the end flap portion 34 of the unitary body member 14 such that the opposed second end 44 extends outwardly therefrom substantially along the centrally disposed longitudinal axis of the unitary body member 14. Similarly, the first end 46 of the collar fastening strap 40 is secured to the end flap portion 36 of the unitary body member 14 such that the opposed second end 48 of the collar fastening strap 40 extends outwardly from the end flap portion 36 substantially along the centrally disposed longitudinal axis of the unitary body member 14 as shown in FIG. 2. Thus, when the unitary body member 14 is positioned around the neck of the person 12 the collar fastening straps 38, 40 can be tied together to secure the unitary body member 14 to the neck of the person 12. Further, when desired, the collar fastening straps 38, 40 can be disposed under the end flap portions 34, 36 to hide the collar fastening straps 38, 40 when same are in a connected position around the person's neck, and to prevent the opposed second ends 44, 48 of the straps 38, 40 from being exposed which could be detrimental to the person involved in the work situation, especially when working around machinery having moving parts.

It is to be understood that any suitable collar fastening mechanism can be employed, such as the use of VELCRO strips (i.e. a pressure-releasable connecting assembly comprising a male connector member having a flexible base and a plurality of pile-grasping elements, and a female connector member having a flexible base and a pile like surface), snaps, buttons and the like which can be connected to the end flap portions 34, 36 of the unitary body member 14. For example, a second collar fastening mechanism is illustrated in FIG. 7 wherein the second end of one of the collar fastening straps, such as the second end 48 of the collar fastening strap 40 is provided with a buckle 50. Thus, when the unitary body member 14 is positioned around a person's neck the second end 44 of the collar fastening strap 38 can be engaged with the buckle 50 on the second end 48 of the collar fastening strap 40 to secure the comfort collar 10 to the neck of the wearer.

Referring now to FIG. 8, the unitary body member 14 of the comfort collar 10, and the formation and relationship of the first elongated cavity 24 and the second elongated cavity 26 therein is more clearly illustrated. The unitary body member 14 is characterized as having a first side portion 60, a medial portion 62, and a second side portion 64. In fabricating the unitary body member 14 of the comfort collar 10 a loop is made between the first side portion 60 and the medial portion 62 of the unitary body member 14; and the first side portion 60 and the medial portion 62 are connected along a lower, adjacently disposed longitudinally extending edge portion 66 by any suitable means, such as sewing with thread 68. The interconnection of the first side portion 60 and the medial portion 62 thus forms the first elongated cavity 26 in which the elongated insulation member 16 is positioned. Further, the formation of the end flap portions 34, 36 of the unitary body member 14, which forms the sealed end portions of the first elongated cavity 24 can be accomplished by any suitable mechanism, such as by sewing the end portions 30 and 32 with thread, such as thread 70, 72, respectively (see FIGS. 2, 3, 5 and 6) in the same manner that the first side portion 60 and the medial portion 62 are joined along the lower, adjacently disposed longitudinally extending edge portion 66 as heretofore described. The second side portion 64 of the unitary body member 14 is an extension of the medial portion 62 and commences where the first side portion 60 and the medial portion 62 are joined along the lower, adjacently disposed longitudinally extending edge portion 66. The second side portion 64 cooperates with the medial portion 62 for forming the second elongated cavity 26 within the unitary body member 14. The second side portion 64 includes a closure flap portion so that when the second side portion 64 is disposed over an uppermost portion 74 formed by the junction of the first side portion 60 and the medial portion 62 and positioned substantially adjacent the first side portion 60 thereof, the second side portion 64 forms the closure flap for the second elongated cavity 26 formed in the unitary body member 14 substantially as shown in FIG. 8.

The second side portion 64 of the unitary body member 14, which cooperates with the medial portion 62 to form the second elongated cavity 26 and as the closure flap 28 for sealing the second elongated cavity 26, is moveable between a first or open position (as shown in FIGS. 3, 5 and 6) and a second or closed position (as shown in FIGS. 2 and 8). When the closure flap 28 is in the first position access is readily available to the second elongated cavity 26 of the towel 14 because the second side portion 64 of the unitary body member 14 extends in a direction away from the first side portion 60 of the unitary body member 14. On the other hand, when the closure flap 28 is in the second position the second side portion 64 of the unitary body member 14 is disposed over the uppermost portion 74 formed by the junction of the first side portion 60 and the medial portion 62, and the closure flap 28 is disposed substantially adjacent the first side portion 60 of the unitary body member 14 (substantially as shown in FIG. 2 and 8) such that the second side portion 64 substantially closes off the second elongated cavity 26 of the unitary body member 14 and secures the coolant containing packets, such as coolant packet 22, within the second elongated cavity 26.

The second elongated cavity 26 formed in the comfort collar 10 by the medial portion 62 and the second side portion 64 of the unitary body member 14 is desirably divided into a plurality of cavity segments, such as cavity segments 80, 82 and 84 so as to form pockets for receiving and securing the cooling packets 18, 20 and 22 with the unitary body member 14 of the comfort collar 10. Any suitable means can be employed to divide the second cavity 26 of the comfort collar 10 into the cavity segments 80, 82 and 84, such as by sewing the unitary body member 14 with thread to define the boundaries of each of such cavity segments, such as with threads 86 and 88. The exterior end portions of the cavity segments 80 and 84 which define the inner boundaries of the end flap portions 34, 36 of the comfort collar 10 are formed by sewing the unitary body member 14 at the appropriate position with threads 70 and 72, respectfully, as heretofore described.

Referring now to FIGS. 4, 5, 6, and 8, the coolant containing packets 18, 20 and 22 employed for providing the cooling effect of the comfort collar 10 are shown. Each of the coolant containing packets 18, 20 and 22 are identical in construction, and are provided with a configuration sufficient to be positioned within the cavity segments 80, 82 and 84 formed in the comfort collar 10. Since the configuration of the coolant containing packets 18, 20 or 22 are substantially identical in configuration, only coolant containing packet 22 will be described in detail with referece to FIGS. 4 and 8 of the drawing. The coolant containing packet 22 is illustrated as a rectangularly shaped packet having a sealable fluid-impervious pliable body member 90 which is positionable within the cavity segment 84 of the second elongated cavity 26. A freezable fluid 92, such as water, is placed in the fluid-impervious pliable body member 90 of the coolant containing packet 22; and the coolant containing packet 22 is sealed, either temporarily, such as by zip locking, or permanently with a heat sealing device so that the freezable fluid 92 is contained within the fluid-impervious pliable body member 90. The fluid-impervious pliable body member 90 can then be formed in the desirable shape prior to freezing the fluid 92 therein such that upon insertion of the coolant containing packet 22 within the cavity segment 84 of the second elongated cavity 26 the configuration of the frozen fluid 92, and thus the packet 22 conform to the desired shape for placement of the comfort collar 10 around the neck of the person 12.

Once the cooling packets 18, 20 and 22 have been positioned in their respective cavity segments 80, 82 and 84 of the second elongated cavity the second side portion 64 of the unitary body member 14 is folded over the upper portion 74 of the first side portion 60 and the medial portion 62 such that the second side portion 64 is disposed substantially adjacent the first side portion 60 and substantially seals the cavity segments 80, 82 and 84 substantially as shown in FIGS. 2 and 8. In order to prevent the undesired removal of the coolant containing packets 18, 20 and 22 from the cavity segments 80, 82 and 84 of the elongated second cavity formed within the comfort collar 10, the second side portion 62 is secured to the first side portion 60 of the unitary body member 14 by and suitable means, such as ties, buttons, "VELCRO" (i.e. a pressure-releasable connecting assembiy comprising a male connector member having a flexible base and a plurality of pile-grasping elements, and a female connector member having a flexible base and a pile like surface), or a plurality of snap mechanisms 93 as illustrated in FIGS. 1, 2, 3, 5, 6 and 8. The snap mechanisms 93, which comprise a male component and a female component are well known in the art. Thus, no further description of such snap components is believed necessary.

Referring now to FIG. 6, the improved comfort collar 10 further comprises a plurality of insulation insert members 94, 96, and 98. The insulation insert members 94, 96 and 98 are positionable within the cavity segments 80, 82 and 84, respectively, of the second elongated cavity 26 formed in the unitary body member 14 so as to be positioned between the neck of the wearer 12 and the cooling packets 18, 20 and 22 disposed in the cavity segments 80, 82 and 84 when the comfort collar 12 is secured around the wearer's neck.

The comfort collar 10 described above is a simple, economical and convenient way to dissipate the heat from one's body so as to enable the person to work comfortably, even when subjected to high ambient heat conditions. Further, the comfort collar 10 of the present invention is well adapted to carry out the objects and attain the ends and advantages mentioned as well as those inherent therein. It will be understood that numerous changes may be made in the comfort collar 10 which will readily suggest themselves to those skilled in the art and which are encompassed within the spirit of the invention as defined in the appended claims.

What is claimed is:

1. An improved comfort collar adapted to be worn about the neck of a person subjected to high ambient heat conditions comprising:
  (a) a unitary body member formed of a water-absorbent textile material and having a first and a second elongated cavity formed therein, the second cavity being divided into a plurality of segments, the unitary body member adapted to substantially encompass and form a continuous collar about the neck of the wearer, the unitary body member further characterized as having a first side portion, a medial portion and a second side portion, the first side portion and the medial portion being connected along a lower, adjacently disposed longitudinally extending edge so as to define the first elongated cavity therebetween, the second side portion of the body member extending from the medial portion and cooperating with the medial portion to define the second elongated cavity therebetween, the second side portion of the body member further provided with a closure flap portion positionable in one of a first position and a second position, in the first position the closure flap portion extending away from the medial portion of the unitary body member such that substantially unrestricted access is permitted to the second elongated cavity, in the second position the closure flap portion extending over an uppermost portion of the body member defining the first elongated cavity such that the closure flap portion is disposed substantially adjacent the first side portion of the body member and closes off the second elongated cavity;
  (b) an elongated insulation member disposed within the first elongated cavity so as to be substantially encapsulated therein, the elongated insulation member being fabricated of a sufficiently pliable material such that the insulation member is adapted to substantially encompass the neck of the wearer; and, (c) cooling means disposable within the segments of the second elongated cavity for providing a comfort zone to receive heat from the wearer's neck.

2. The improved comfort collar of claim 1 further comprising:

fastening means for securing the closure flap portion of the second side portion of the body member to the first side portion when the closure flap portion of the second side portion is in the second position.

3. The improved comfort collar of claim 2 wherein said first and second cavities terminate a selected distance from opposite end portions of said body member so as to provide each end portion of said body member with an end flap, and wherein said collar further comprises collar fastening means supported by each of the end flaps for securing the collar about the neck of the wearer.

4. The improved comfort collar of claim 3 wherein said collar fastening means comprises a pair of straps, each of said straps having a first end and a second end, the first end of one of the straps connected to one of said end flaps and the first end of the other of the straps connected to the other of said end flaps such that when the body member of the collar is disposed around the neck the second ends of the straps are connectable for securing the collar around the wearer's neck.

5. The improved comfort collar of claim 4 wherein the collar fastening means further comprises a buckle connected to the second end of one of the straps, said buckle adapted to receive the second end of the other of said straps in locking engagement.

6. The improved comfort collar of claim 4 wherein said cooling means comprises a plurality of cooling packets, one of said cooling packets disposable within each segment of said second cavity.

7. The improved comfort collar of claim 6 wherein each of said cooling packets comprises:

a sealable, fluid-impervious pliable body member having a fluid-receiving cavity defined therein; and a substantially frozen fluid disposed within the fluid-receiving cavity.

8. The improved comfort collar of claim 6 further comprising:

a plurality of insulation insert members, one of said insulation insert members disposable within each of the segments of the second cavity, the cooling packet being positioned within the segment of the second cavity such that the cooling packet is disposed between the insulation insert and a portion of the elongated insulation member of the first cavity disposed substantially adjacent the segment of the second cavity containing the cooling packet and the insulation insert member.

* * * * *